United States Patent
Brandenburg et al.

(10) Patent No.: US 6,417,382 B2
(45) Date of Patent: Jul. 9, 2002

(54) PROCESS FOR PREPARING ARYL-IMINOMETHYL-CARBAMINO ACID ESTERS

(75) Inventors: Joerg Brandenburg, Wiesbaden Dotzheim; Rolf Schmid, Baltringen; Rainer Soyka, Biberach; Ralf Anderskewitz, Bingen; Rolf Bauer; Rainer Hamm, both of Ingelheim; Jutta Kroeber, Bingen, all of (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 09/757,253

(22) Filed: Jan. 9, 2001

Related U.S. Application Data

(60) Provisional application No. 60/177,378, filed on Jan. 24, 2000.

(30) Foreign Application Priority Data

Jan. 12, 2000 (DE) .......................................... 100 00 907

(51) Int. Cl.[7] .............................................. C07C 309/00
(52) U.S. Cl. .......................................... 558/44; 560/27
(58) Field of Search ........................... 560/24; 514/637; 564/244, 247; 860/24, 29, 27; 558/423, 416, 44

(56) References Cited

U.S. PATENT DOCUMENTS 5,246,965 A    9/1993   Main
5,731,332 A  *  3/1998   Anderskewitz et al.

FOREIGN PATENT DOCUMENTS

EP         0 518 818 A2   12/1992
WO         WO96 02497 A1   2/1996

* cited by examiner

Primary Examiner—Johann Richter
Assistant Examiner—Paul A. Zucker
(74) Attorney, Agent, or Firm—Robert P. Raymond; Alan R. Stempel; Mary-Ellen M. Devlin

(57) ABSTRACT

The invention relates to a process suitable for large-scale industrial use for preparing compounds of general formula (I)

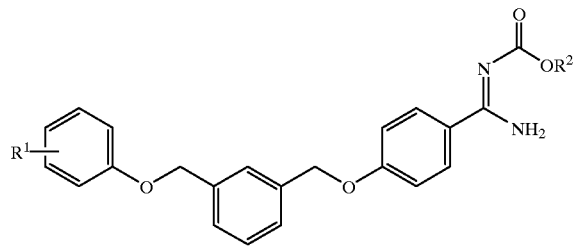

(I)

wherein:

$R^1$ denotes a group selected from among methyl, ethyl, propyl, cyclopentyl, cyclohexyl, phenyl, benzyl and —C(Me$_2$)phenyl, each of which is optionally mono-, di- or trisubstituted by hydroxy; and, $R^2$ denotes a group selected from among methyl, ethyl, propyl and benzyl.

7 Claims, No Drawings

PROCESS FOR PREPARING ARYL-IMINOMETHYL-CARBAMINO ACID ESTERS

RELATED APPLICATIONS

Benefit of U.S. Provisional Application Serial No. 60/177,378, filed on Jan. 24, 2000 is hereby claimed.

FIELD OF THE INVENTION

The invention relates to a process for the production of compounds of general formula (I)

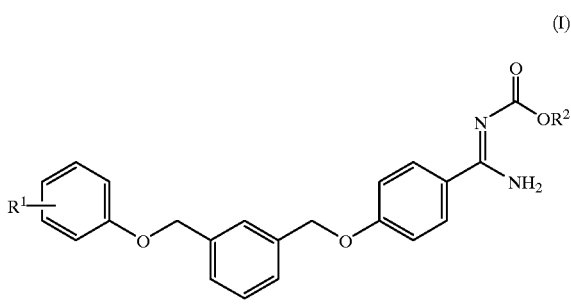

(I)

wherein the groups $R^1$ and $R^2$ may have the meanings given in the specification and claims.

BACKGROUND OF THE INVENTION

From International Patent Application WO 96/02497, benzamidines and aryl-iminomethylcarbamino acid esters are known which are highly effective as pharmaceutical compositions with an $LTB_4$-antagonistic activity. Compounds of general formula (I) are of particular importance.

The problem of the present invention is to provide a process which can be used for industrial-scale synthesis of compounds of general formula(I) in high yields and with end products of high purity.

DETAILED DESCRIPTION OF THE INVENTION

To solve the problem mentioned above, the invention provides a process for preparing compounds of general formula (I)

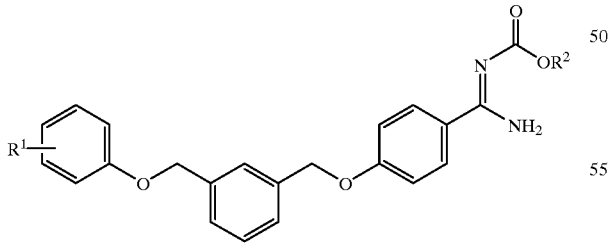

(I)

wherein
$R^1$ denotes a group selected from among methyl, ethyl, propyl, cyclopentyl, cyclohexyl, phenyl, benzyl and —C(Me$_2$)phenyl, each of which may be mono-, di- or trisubstituted by hydroxy;
$R^2$ denotes a group selected from among methyl, ethyl, propyl and benzyl, characterised in that a compound of general formula (II)

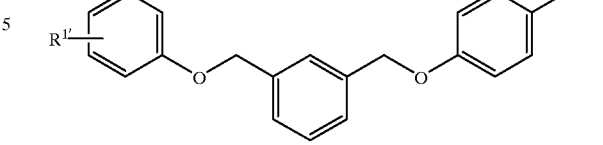

(II)

wherein
$R^{1'}$ denotes a group selected from among methyl, ethyl, propyl, cyclopentyl, cyclohexyl, phenyl, benzyl and —C(Me$_2$)phenyl, each of which may be mono-, di- or trisubstituted by a group —O—PG, the group —O—PG denoting a protected hydroxyl function selected from among methoxymethyloxy, 2-methoxyethoxymethyloxy, 1-ethoxyethyloxy, 2-tetrahydropyranyloxy, 1-butoxyethyloxy, tert.-butyloxy, benzyloxy and 4-methoxybenzyloxy, is first reacted in an ethereal or aromatic solvent with an alkali metal hexaalkyldisilazane and is then treated with a compound of formula (III)

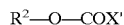

$R^2$—O—COX'  (III)

wherein
$R^2$ is as hereinbefore defined and
X' denotes chlorine, bromine or —O—$R^2$, after working up using an acid of formula HY a compound of formula (IV) wherein the groups $R^1$ and $R^2$ are as hereinbefore defined and Y denotes any desired acid group,
is isolated and from this the compound of formula (I) is liberated.

The compounds of formulae (I) and (IV) also include the corresponding tautomers of formulae (I-T) and (IV-T):

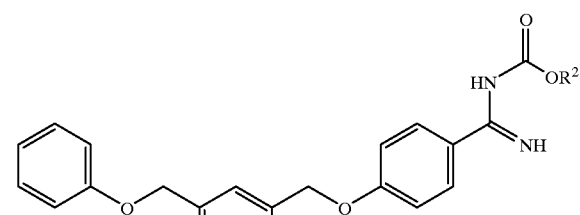

(I-T)

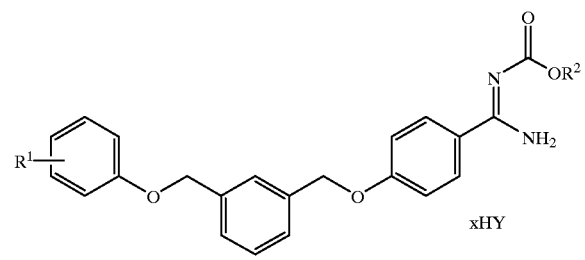

(IV-T)

The term "alkali metal hexaalkyldisilazane" as used above and hereinafter to denote the reagent which is reacted with the compound of formula (II) generally designates a compound of formula (VIII)

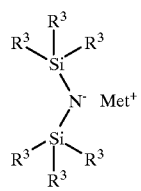

(VIII)

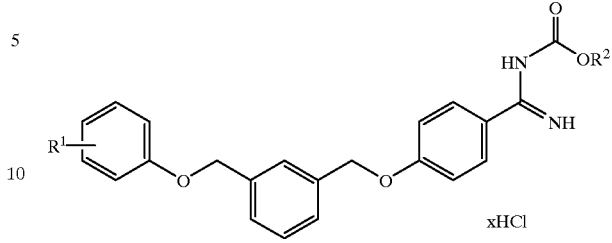

(IVA)

wherein

Met denotes an alkali metal, preferably lithium, sodium or potassium, particularly lithium, and $R^3$ independently in each case denotes a $C_{1-4}$-alkyl group, preferably methyl or ethyl, especially methyl.

Most particularly preferred are lithium hexamethyldisilazane, sodium hexamethyldisilazane and potassium hexamethyldisilazane, particularly lithium hexamethyldisilazane.

The term "subsequent reaction" with a compound of formula (III) covers both procedures in which the product of the reaction of the compound of formula (II) with the alkali metal hexamethyldisilazane is reacted with the compound of formula (III) directly, without any further intermediate reaction, and also procedures in which the free amidine base is liberated in the mean time from the product formed. Preferably, the product of the reaction of the compound of formula (II) with the alkali metal hexamethyldisilazane is reacted with the compound of formula (III) directly, especially in a "one-pot synthesis".

A preferred process for preparing compounds of general formula (I) is one wherein $R^1$ denotes a group selected from among phenyl, benzyl and —C(Me$_2$)phenyl, each of which may be mono- or disubstituted, preferably monosubstituted by hydroxy;

$R^2$ denotes a group selected from among ethyl, propyl and benzyl, characterised in that a compound of general formula (II)

wherein $R^{1'}$ denotes a group selected from among phenyl, benzyl and —C(Me$_2$)phenyl, each of which may be mono- or disubstituted, preferably monosubstituted by a group —O—PG, the group —O—PG denoting a protected hydroxyl function selected from among methoxymethyloxy, 2-methoxyethoxymethyloxy, 1-ethoxyethyloxy, 2-tetrahydropyranyloxy, 1-butoxyethyloxy, tert.-butyloxy, benzyloxy and 4-methoxybenzyloxy, preferably 2-tetrahydropyranyloxy, is first reacted in an ethereal or aromatic solvent with an alkali metal hexaalkyldisilazane and then treated with a compound of formula (III)

$$R^2—O—COX' \qquad (III)$$

wherein $R^2$ is as hereinbefore defined and

X' denotes chlorine, bromine or —O—$R^2$, after working up with aqueous hydrochloric acid a compound of formula (IVA)

wherein the groups $R^1$ and $R^2$ are as hereinbefore defined is isolated and from this the compound of formula (I) is liberated.

Particularly preferred is a process for preparing compounds of general formula (I) wherein $R^1$ denotes —C(Me$_2$)phenyl which may optionally be monosubstituted by hydroxy and $R^2$ denotes ethyl, characterised in that a compound of general formula (II) wherein $R^{1'}$ denotes —C(Me$_2$)phenyl, which may optionally be monosubstituted by a group —O—PG, the group —O—PG denoting a protected hydroxyl function selected from among methoxymethyloxy, 2-tetrahydropyranyloxy, 1-butoxyethyloxy, tert.-butyloxy, benzyloxy and 4-methoxybenzyloxy, preferably 2-tetrahydropyranyloxy, is first reacted in an ethereal or aromatic solvent with an alkali metal hexaalkyldisilazane and then treated with a compound of formula (III)

$$R^2—O—COX' \qquad (III)$$

wherein $R^2$ is as hereinbefore defined and

X' denotes chlorine, bromine or —O—$R^2$, preferably chlorine, after working up with aqueous hydrochloric acid a compound of formula (IVA) wherein the groups $R^1$ and $R^2$ are as hereinbefore defined is isolated and from this the compound of formula (I) is liberated.

In a particularly preferred embodiment of the process according to the invention, the compound of formula (II) is prepared in a process comprising the following steps:

(a) reacting $C_{1-4}$-alkyl 3-halomethylbenzoates with 4-hydroxybenzonitrile in the manner of a Wilkinson ether synthesis;

(b) reductively converting the resulting alkyl 3-(4-cyanophenoxy)benzoates of formula (VII)

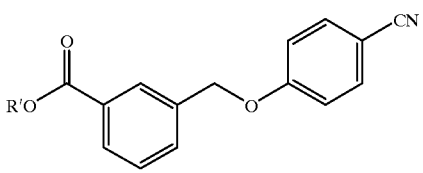

(VII)

wherein R' denotes $C_{1-4}$-alkyl, into a compound of formula (V)

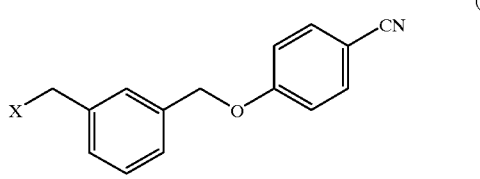

(V)

wherein X denotes hydroxy;
(c) optionally treating the compound of formula (V) wherein X denotes hydroxy with a halogenating reagent or a sulphonic acid chloride;
(d) reacting the compound of formula (V) wherein X denotes hydroxy, chlorine, bromine, mesylate, triflate or tosylate, with a phenol derivative of formula (VI)

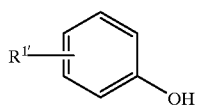

(VI)

wherein $R^{1'}$ denotes a group selected from among methyl, ethyl, propyl, cyclopentyl, cyclohexyl, phenyl, benzyl and —C(Me$_2$)phenyl, each of which is optionally mono-, di- or trisubstituted by a group —O—PG, the group —O—PG denoting a protected hydroxyl function selected from among methoxymethyloxy, 2-methoxyethoxymethyloxy, 1-ethoxyethyloxy, 2-tetrahydropyranyloxy, 1-butoxyethyloxy, tert.-butyloxy, benzyloxy and 4-methoxybenzyloxy,; optionally in the form of the corresponding sodium or potassium phenoxides, under basic reaction conditions, preferably in a polar organic solvent.

The hydrochlorides of formula (IVA) are of central importance in the process according to the invention for preparing the compounds of general formula (I). They are obtained directly in high yields as readily crystallising salts, from which by-products and/or impurities can easily be removed by crystallisation. Accordingly, one aspect of the present invention relates to intermediate products of general formula (IVA)

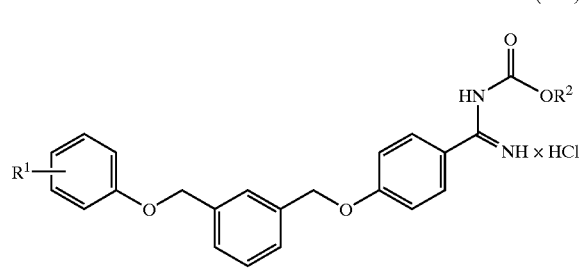

(IVA)

wherein the groups $R^1$ and $R^2$ may be as hereinbefore defined.

Of the compounds of general formula (IVA) the compound ethyl{[4-(3-{4-[1-(4-hydroxy-phenyl)-1-methyl-ethyl]-phenoxymethyl}-benzyloxy)-phenyl]-imino-methyl}-carbaminate hydrochloride is particularly preferred.

The compounds of general formula (II)

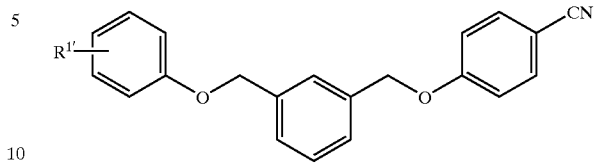

(II)

wherein $R^{1'}$ may be as hereinbefore defined are obtained according to the invention by reacting a compound of formula (V)

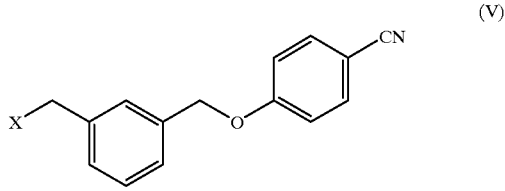

(V)

wherein X denotes hydroxy, chlorine, bromine, mesylate, triflate, benzenesulphonate or tosylate, with a compound of formula (VI)

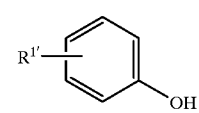

(VI)

wherein $R^{1'}$ may be as hereinbefore defined and wherein the compound of formula (VI) may optionally also be used in the form of the sodium and potassium phenoxides thereof, under basic reaction conditions in a polar organic solvent.

It is preferred to prepare compounds of general formula (II) wherein $R^1$ may be as hereinbefore defined by reacting a compound of formula (V) wherein X denotes hydroxy, chlorine or mesylate, more preferably hydroxy or chlorine, most preferably chlorine, with a compound of formula (VI) wherein $R^{1'}$ may be as hereinbefore defined and wherein the compound of formula (VI) is used in the form of the alkali metal phenoxides thereof, preferably in the form of the sodium phenoxides thereof.

When the compounds of general formula (I) are synthesised according to the invention, the intermediate products of general formula (V) are of central importance. In another aspect, therefore, the present invention relates to the compounds of general formula (V)

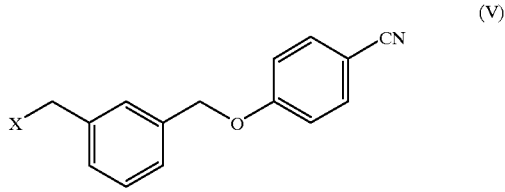

(V)

as such, wherein X may be as hereinbefore defined and most preferably may denote hydroxy or chlorine.

The compound of formula (VII), one of the starting compounds, is also of particular importance in the synthesis according to the invention of the compounds of general formula (I). Therefore, in another aspect, the present invention relates to the compounds of formula (VII)

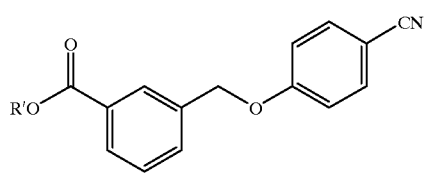

(VII)

as such, wherein R' denotes $C_{1-4}$-alkyl, preferably methyl or ethyl, most preferably methyl.

In order to perform the process for preparing the compounds of general formula (I) according to the invention starting from the nitriles of general formula (II) the following method is used:

A compound of general formula (II) is slowly metered into a solution of the alkali metal hexaalkyldisilazane, preferably lithium bis(trimethylsilyl)-amide, sodium bis(trimethylsilyl)-amide, most preferably lithium bis(trimethylsilyl)-amide, in an ethereal or aromatic organic solvent, preferably in a solvent selected from among tetrahydrofaran, toluene, dioxane, more preferably in tetrahydrofuran or dioxane, most preferably in tetrahydrofuran, preferably with cooling, especially at a temperature between −50° C. and 30° C., more especially at −20° C. to 10° C., most especially at about 0° C. The quantity of the alkali metal hexaalkyldisilazane used is determined by the amount of nitrile of formula (II) used. At least 1 mol, preferably 1.01 to 1.15 mol of alkali metal hexaalkyldisilazane is used per mol of nitrile of formula (II). The quantity of ethereal solvent used is between 0.7 and 1.5, preferably 0.9 to 1.3 kg per mol of compound of formula (II) used.

After all the compound of formula (II) has been added the resulting suspension is stirred at constant temperature, optionally at a temperature of up to 40° C., preferably at about 20–25° C. over a period of 6 to 24 hours, preferably 8 to 18 hours. The stirring is preferably continued for 10 to 12 hours. During this time the solid which was initially in suspension may go into solution.

The mixture can then optionally be diluted either with additional ethereal solvent or with a nonpolar organic solvent, preferably with an aromatic organic solvent. A solvent selected from among toluene, benzene, cyclohexane, methylcyclohexane or xylene is preferably used, of which toluene and xylene are particularly preferred, toluene being most preferred. If the mixture is diluted, it is sufficient to add up to 0.5 L, preferably up to 0.3 L of solvent per mol of compound of formula (II) used.

The reaction mixture is heated to a reaction temperature of between −50° C. and 20° C., more especially −20° C. to 10° C., most preferably −10 to 0° C. before the addition of the compound of general formula (III). Then the compound of formula (III) is added, in an amount of at least 1 mol, preferably 1.05 to 1.3 mol, more particularly 1.1 to 1.2 mol, per mol of compound of formula (II) used.

After the reaction is complete, the product is hydrolysed by the addition of an acid of formula HY, preferably an inorganic or organic acid such as hydrochloric acid, sulphuric acid, phosphoric acid, acetic acid, trifluoroacetic acid, oxalic acid and fumaric acid, particularly aqueous hydrochloric acid. About 1 mol of acid, particularly hydrochloric acid, is used per mol of the compound of formula (II) originally used. According to the invention, it is preferable to add dilute hydrochloric acid (preferably 8-15%, more especially 10–12% strength).

After a period of about 10 minutes to 1 hour the aqueous lower phase is separated off and an organic solvent selected from among acetone, methylisobutylketone, methylethylketone, optionally a mixture of two of the above solvents, most preferably a mixture of acetone and methylisobutylketone in a ratio of 3-1:1, most preferably in a ratio of 2.5-1.5:1, is added to the organic phase. Crystallisation of the compounds of formula (IVA) is initiated by the addition of aqueous hydrochloric acid. About 1 to 1.2 mol of hydrochloric acid is used per mole of the compound of formula (II) originally used. It is preferred according to the invention to add preferably 32–37%, most preferably 37% hydrochloric acid. The compounds of formula (IV) are separated from the reaction mixture by conventional methods, e.g. by centrifugation, washed with an organic solvent selected from among acetone, methylisobutylketone, methylethylketone or a carboxylic acid ester, preferably acetone, and dried.

The release of the compounds of formula (I) from the acid addition salts of formula (IV), particularly from the hydrochlorides of formula (IVA), is generally carried out with basic reactants under reaction conditions which are as neutral as possible, preferably in the presence of buffer systems, according to the method described hereinafter:

An organic solvent selected from among acetone, methylisobutylketone, methylethylketone, tetrahydrofuran or a carboxylic acid ester, preferably acetone, and then a compound of formula (IV) are added to a solution of trisodium citrate dihydrate, sodium hydroxide, potassium hydroxide, alkali or alkaline earth metal salts of organic or inorganic weak acids, preferably trisodium citrate dihydrate, trisodium citrate or sodium hydroxide, most preferably trisodium citrate dihydrate in water at 0-40° C., preferably at 20–25° C., particularly at about 20° C. About 1–2 mol, preferably about 1.5 mol of the sodium or potassium citrate used and about 1 to 3 L of the abovementioned organic solvent, preferably about 2 L, are used per mol of compound of formula (IV) put in. The mixture is stirred at constant temperature over a period of 20 minutes to 2 hours, preferably 1–1.2 hours.

When strong bases such as sodium hydroxide are used, the method of addition may be reversed if desired. The crystalline product is separated off by filtration, for example, washed with water to remove any salt, and with the abovementioned organic solvent and finally dried.

The compounds of general formula (II) may be obtained by reacting a compound of formula (V) with a compound of formula (VI), as already mentioned. According to the invention, the following procedure may be used.

The compound of formula (V) wherein X denotes hydroxy is dissolved in an organic solvent, if possible an aprotic-polar organic solvent, preferably N,N-dimethylacetamide, acetone, methylethylketone, methylisobutylketone, N-methylpyrrolidone, N,N-dimethylformamide, tetraalkylurea, most preferably in N,N-dimethylacetamide. 0.5 to 1.0, preferably about 0.7 L of solvent are used at this point per mol of starting compound according to the invention. Then the solution thus obtained is cooled to a temperature of <10° C., preferably to a temperature between +5° C. and −20° C., most preferably to about −10° C. to 0° C. Then a suitably substituted sulphonic acid chloride, optionally the abovementioned organic solvent, an organic base, optionally the abovementioned organic solvent and the aqueous solution of an inorganic base are added one after the other. A suitably substituted sulphonic acid chloride according to the invention might be methanesulphonic acid chloride, para-toluenesulphonic acid chloride, benzenesulphonic acid chloride or trifluoromethanesulphonic acid chloride. Preferably, methanesulphonic acid chloride is used. The organic bases may be, for example, dimethylaminopyridine, pyridine, methylpyridine, tert. amines, e.g. trimethylamine, triethylamine, diisopropylethylamine, or cyclic amines such as N-methylpyrrolidine or DBU (diazabicycloundecene). Preferred organic amines are N-methylpyrrolidine, trimethylamine, triethylamine or diisopropylethylamine, most preferably triethylamine. The organic base is used in at least a stoichiometric amount, based on the starting compound of formula (V). Preferably, the organic base is used in an excess of 10–50 mol %, most preferably in about a 30% excess in relation to the compound of formula (V) used. The aqueous solution of an organic base used will usually be an alkali metal or alkaline earth metal hydroxide solution, the alkali metal hydroxide solutions being preferred. The aqueous solutions of potassium hydroxide and sodium hydroxide are particularly important according to the invention. Usually, 20-50% solutions of the abovementioned inorganic hydroxides are used. More concentrated solutions such as, for example, 45% solutions are preferred according to the invention. Based on the compound of formula (V) used, the inorganic base is used in at least a stoichiometric amount, preferably in an excess of 50–100 mol %. The inorganic base is particularly preferably used in an excess of about 75 mol %, based on the compound of formula (V) added. If desired, the reaction mixture may be diluted after the addition of the suitably substituted sulphonic acid chloride or the organic base by the addition of the abovementioned organic solvent. In this case, 2–10%, preferably about 5% of the quantity of solvent put in initially is added.

In any case, after all the aqueous solution of the inorganic base has been added, the reaction mixture is diluted with the organic solvent mentioned above. About 0.5 to 1.0 L, preferably between 0.7 and 0.8 L of the solvent used are added, per mol of starting compound of formula (V) used. Then alkoxides or metal salts of formula (VI) are added. The sodium and potassium phenoxides which may be derived from the compounds of formula (VI) are preferably used. According to the invention, stoichiometric quantities, optionally substoichiometric quantities or an excess of the compound (VI) may be added, based on the educt of formula (V). After all the compound (VI) has been added, the reaction is continued for a period of about 1–3 hours, preferably about 1.5 to 2 hours at a temperature of 5–35° C., preferably at about 25° C., and finally stirred for a period of about 1–3 hours, preferably about 1.5–2 hours at a temperature of 50–100° C., preferably at about 70–90° C. After the reaction has ended the product of formula (II) is crystallised by the addition of a suitable polar solvent selected from among the lower alcohols and water.

In order to obtain high yields of particularly pure products, it has proved preferable according to the invention to add, for the crystallisation, a solvent mixture consisting of a nonpolar organic solvent, preferably xylene or toluene, most preferably toluene, a polar organic solvent, preferably a lower alcohol such as methanol, ethanol, butanol or isopropanol, especially isopropanol and water. The ratio by volume of nonpolar to polar organic solvent to water can vary within the range from 1:7–10:5–8, preferably 1:8–9:6–7. By cooling to below 50° C., preferably to about 30° C., the crystallisation of the product of formula (II) is completed. After isolation, the crystallised product is optionally washed with the abovementioned lower alcohol and with water.

If the compounds of formula (II) are to be obtained from the compounds of formula (V) wherein X has a meaning other than hydroxy, the following procedure may be used according to the invention.

The sodium or potassium phenoxide derived from the compounds of formula (VI) is taken up in water together with a compound of formula (V), mixed with a nonpolar organic solvent and optionally reacted under phase transfer conditions. The phase transfer catalysts which may be used according to the invention include the quaternary ammonium salts, preferably the halides, sulphates or hydroxides of tetradecyltrimethylammonium, hexadecyltrimethylammonium, tetrabutylammonium, tributylmethylammonium or triethylbenzylammonium. The nonpolar organic solvent may be a chlorinated hydrocarbon such as methylene chloride or preferably, according to the invention, an aromatic hydrocarbon such as benzene, toluene, xylene, preferably toluene. The compounds of formula (V) and (VI) are used in a virtually stoichiometric ratio, and if desired one of the two reactants may also be used in a slight excess (e.g. 15%). The amount of solvent to be used depends on the quantity of educt put in. Between 1 and 2 L of water and between 0.3 and 1.0 L of the organic solvent, preferably between 1.5 and 1.8 L of water and 0.5 to 0.7 L of the organic solvent are used per mol of compound of formula (VI) put in. The reaction is carried out with intensive stirring over a period of 3 to 9, preferably 5 to 7 hours at a temperature of 50 to 100° C., preferably at 70 to 80° C. Then, to crystallise the product, a polar organic solvent, preferably a lower alcohol, most preferably isopropanol is added to the separated organic phase. By cooling to below 50° C., preferably to about 30° C., the crystallisation of the product of formula (II) is completed. After being isolated, the crystallised product of formula (II) is optionally washed with the abovementioned lower alcohol and with water.

The starting compounds of formula (V)

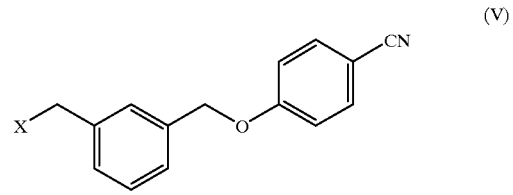

(V)

which, as already mentioned, relate to one aspect of the present invention, may be prepared analogously to methods of synthesis known per se. The compound of formula (V) wherein X denotes hydroxy may be prepared by reacting methyl 3-halomethyl-benzoates with 4-hydroxybenzonitrile, for example, in a Wilkinson ether synthesis. The methyl 3-(4-cyano-phenoxy)-benzoate (VII) thus obtained can be reductively converted into the compound of general formula (V) wherein X=hydroxy (=4-(3-hydroxymethyl-benzyloxy)-benzonitrile) by the analogous use of current standard procedures.

The compounds of formula (V) wherein X denotes chlorine or bromine may be prepared analogously to methods of synthesis known per se from the compound of formula (V) wherein X denotes hydroxy, using common halogenation reagents such as, for example, thionylchloride, phosphorus oxychloride or phosphorus pentachloride, methanesulphonic acid chloride, benzenesulphochloride, preferably thionylchloride or methanesulphonic acid chloride.

The compounds of formula (V) wherein X denotes mesylate, triflate or tosylate may be prepared analogously to methods of synthesis known per se from the compound of formula (V) wherein X denotes hydroxy, by reacting with the appropriate sulphonic acid chlorides in aprotic, preferably polar organic solvents, preferably selected from among dichloromethane, N,N-dimethylacetamide, dimethylformamide, acetonitrile, N-methylpyrrolidone, tetraalkylurea in the presence of organic bases, preferably selected from among dimethylaminopyridine, pyridine, methylpyridine, N-methylpyrrolidine, trimethylamine, triethylamine, diisopropylethylamine and DBU (diazabicycloundecene).

The following Examples serve to illustrate methods of synthesis according to the invention, carried out by way of example, for preparing the compound of formula (I). They must be considered as possible methods given by way of example, without restricting the invention to their content.

EXAMPLE 1

Methyl 3-(4-cyano-phenoxymethyl)-benzoate 10.00 kg (43.6 mol) of methyl 3-(bromomethyl)benzoate and 5.21 kg (43.74 mol) of 4-hydroxybenzonitrile are dissolved in 100 liters of acetone and stirred with 8.4 kg (60.7 mol) of potassium carbonate in the presence of 0.1 kg of sodium iodide for about 4 h under reflux conditions. Then 35 liters of acetone are distilled off and 100 liters of water are added at reflux conditions. The reaction mixture is cooled to 20° C. and the crystallisation is completed by the addition of another 30 liters of water. The crystals formed are separated off, washed with 50 liters of water and dried in vacuo.

Yield: 11.1 kg (95%) of methyl 3-(4-cyano-phenoxymethyl)-benzoate;

Melting point 109 . . . 112° C., white solid,

TLC (silica gel 60 F254-ready-made plate (Merck): Rf=0.5 (toluene:acetone=9:1)

EXAMPLE 2

4-(3-hydroxymethyl-benzyloxy)-benzonitrile 20.05 kg (26.7 mol) of methyl 3-(4-cyano-phenoxymethyl)-benzoate are dissolved in 100 liters of THF and 40 liters of methanol. At 40 to 45° C., 8.51 kg of sodium boranate are added in batches. The reaction is completed by stirring the reaction mixture at 61 to 63° C. for about 5 hours. The reaction mixture is then cooled to 25° C. and 90 liters of a 15% sodium hydroxide solution are added. After stirring, the aqueous supernatant is separated off and mixed with 30 liters of a 22.5% sodium hydroxide solution. After stirring, the aqueous supernatant is separated off and from this about 100 liters of solvent are distilled off at a sump temperature of 63 to 75° C. The distillation residue is crystallised by the addition of 20 liters of isopropanol at 50 to 60° C. and 150 liters of water at 40 to 50° C. After the suspension has been cooled to 20 to 30° C. the crystals are separated off, washed with 60 to 100 liters of water and batchwise with 25 liters of cold isopropanol and dried in vacuo.

Yield: 15.8 kg (88%) of 4-(3-hydroxymethyl-benzyloxy)-benzonitrile;

Melting point (DSC): 110–115° C., white solid

IR: 3444/cm (OH band); 2229/cm (CN band)

EXAMPLE 3

4-(3-Chloromethyl-benzyloxy)-benzonitrile

Variant A:

7.18 g (30 mmol) of 4-(3-hydroxymethyl-benzyloxy)-benzonitrile are dissolved in 80 ml of dichloromethane, mixed with 4.13 g (35 mmol) of thionylchloride and 0.1 g of DMF and stirred while heating to 40° C. until the development of gas has ceased. After cooling, the organic reaction mixture is washed successively with water and dilute sodium hydroxide solution and crystallised by evaporation.

Yield: 6.8 g (88%) of 4-(3-chloromethyl-benzyloxy)-benzonitrile;

TLC (silica gel 60 F254-ready-made plate (Merck): Rf=0.9 (toluene-acetone=9:1), Rf=0.44 (toluene)

Variant B:

7.18 g (30 mmol) of 4-(3-hydroxymethyl-benzyloxy)-benzonitrile are dissolved in 22 ml of N,N-dimethylacetamide, mixed with 4.47 g (39 mmol) of methanesulphonic acid chloride and 3.95 g (39 mmol) of triethylamine and stirred for 10 hours at 20–30° C. Then the triethylammonium chloride precipitated is filtered off, the filtrate is mixed with 30 ml of isopropanol and the desired 4-(3-chloromethyl-benzyloxy)-benzonitrile is crystallised by the metered addition of 30 ml of water. The suspension is stirred for 15 min at 10° C. and filtered. The crystals are washed with a mixture of 5 ml of isopropanol and 20 ml water and dried at 20° C. in vacuo. Yield: 6.8 g (88%) of 4-(3-chloromethyl-benzyloxy)-benzonitrile Melting point: 65–68° C.

EXAMPLE 4

Sodium-4-{1-methyl-1-[4-tetrahydro-pyran-2-yloxy)-phenyl]-ethyl}-phenoxide 121.8 kg of bisphenol A are suspended in 480 l of toluene and 46 l of THF. After the addition of the catalyst (1.3 kg of 37% hydrochloric acid), 44.9 kg of 3,4-dihydro-2H-pyran are metered in so as not to exceed a temperature of 40° C. The solid then goes into solution. Then the reaction mixture is mixed with 26. 4 kg of 45% sodium hydroxide solution and 260 l of water. The organic upper phase is separated off and about 50 l of solvent are eliminated by distillation. At 30 to 40° C. the organic phase is washed several times with dilute sodium hydroxide solution so that sufficient purity can be achieved (monitored by TLC). If the aqueous lower phase is in the pH range 11.8 to 12.2, excess bisphenol A can easily be separated off.

The toluene phase purified by extraction is mixed with 11 liters of isopropanol and 80 liters of water and heated to 50 to 55° C. By the addition of 47.4 kg of 45% sodium hydroxide solution and cooling the reaction mixture to 20 to 25° C., a crystal suspension is obtained. The crystals are separated by filtration, washed with about 160 l of toluene and then dried in vacuo.

Yield: 96.5 kg (54%) (as the tetra-hydrate)

EXAMPLE 5

Synthesis of 4-[3-(4-{1-methyl-1-[4-(tetrahydro-pyran-2-yloxy)-phenyl]-ethyl}-phenoxymethyl)-benzyloxy]-benzonitrile Variant A: (Starting From Example 2)

28 kg (244 mol) of methanesulphonic acid chloride, 6 liters of N,N-dimethylacetamide, 24.7 kg (244 mol) of triethylamine, 6 liters of N,N-dimethylacetamide, 29.4 kg of 45% sodium hydroxide solution, 143 liters of N,N- dimethylacetamide, 59.7 kg (178.5 mol) of Example 4 (≡sodium-4-{1-methyl-1-[4-tetrahydro-pyran-2-yloxy)-phenyl]-ethyl}-phenoxide, as the tetrahydrate) are metered successively into a solution of 45 kg (188 mol) of 4-(3-hydroxymethyl-benzyloxy)-benzonitrile (Example 2) in 133 liters of N,N-dimethylacetamide at about −10° to 0° C. Then the reaction mixture is stirred for 2 h at 25° C. and for another 1.5 h at 75 to 80° C. After the addition of 32 liters of toluene, 255 liters of isopropanol and 200 liters of water crystallisation begins which is completed by cooling to 30° C. The crystalline product is separated off by filtration, washed with isopropanol and water and then dried in vacuo. Yield: 85 kg (90%) of 4-[3-(4-{1-methyl-1-[4-(tetrahydro-pyran-2-yloxy)-phenyl]-ethyl }-phenoxymethyl)-benzyloxy]-benzonitrile;

Variant B: (Starting From Example 3)

19.4 kg (50 mol) of Example 4 (a sodium-4-{1-methyl-1-[4-tetrahydro-pyran-2-yloxy)-phenyl]-ethyl}-phenoxide, as the tetrahydrate) and 12.2 kg (47.5 mol) of Example 3 (=-4-(3-chloromethyl-benzyloxy)-benzonitrile) are mixed with 85 liters of water, a phase transfer catalyst (e.g.: 2.1 kg (2.5 mol) of a 40% aqueous solution of tetradecyltrimethy-lammonium bromide and 32 liters of toluene and intensively stirred for 6 h at about 80° C. Then 44 liters of isopropanol are metered into the separated organic upper phase, at 50 to 70° C., the crystal suspension obtained is cooled to about 25° C. and filtered. The crystals separated off are washed twice with 25 liters of cold isopropanol and dried in vacuo.

Yield: 22.8 kg (90%) of 4-[3-(4-{1-methyl-1-[4-(tetrahydro-pyran-2-yloxy)-phenyl]-ethyl}-phenoxymethyl)-benzyloxy]-benzonitrile;

EXAMPLE 6

Ethyl {[4-(3-{4-[1-(4-hydroxy-phenyl)-1-methyl-ethyl]-phenoxymethyl}-benzyloxy)-phenyl]-imino-methyl}-carbaminate hydrochloride 132 kg (247 mol) of 4-(3-{4-[1-(4-tetrahydropyranyl-phenyl)-1-methyl-ethyl]-phenoxymethyl}-benzyloxy)-benzonitrile (Example 5) are metered into a solution of 45.5 kg (272 mol) of lithium-bis(trimethylsilyl-)amide in 266 kg of THF at about 0° C. The resulting suspension is stirred for about 10 h at about 25° C. The solid then goes into solution. After the addition of 68 liters of toluene the reaction mixture is cooled to −10° to 0° C. and at this temperature 30.8 kg (284 mol) of ethyl chloroformate are added to the reaction vessel. Once the reaction has finished completely 24.3 kg of 37% hydrochloric acid (diluted with 50 liters of water) are metered in and about 20 min later the aqueous lower phase is separated off. Crystallisation of the intended product is initiated by the subsequent addition of 106 liters of acetone, 48 liters of methylisobutylketone and 24.3 kg of 37% hydrochloric acid.

123 kg (87%) of ethyl {[4-(3-{4-[1-(4-hydroxy-phenyl)-1-methyl-ethyl]-phenoxymethyl}-benzyloxy) phenyl]-imino-methyl}-carbaminate hydrochloride are obtained after centrifuging, washing with acetone and drying in vacuo.

Melting point: 170-175° C.

EXAMPLE 7

Ethyl {[4-(3-{4-[1-(4-hydroxy-phenyl)-1-methyl-ethyl]-phenoxymethyl}-benzyloxy)-phenyl]-imino-methyl}-carbaminate:

466 liters of acetone and 142 kg of ethyl {[4-(3-{4-[1-(4-hydroxy-phenyl)-1-methyl-ethyl]-phenoxymethyl}-benzyloxy)-phenyl]-imino-methyl}-carbaminate hydrochloride (Example 6) are added to a solution of 109 kg of trisodium citrate dihydrate at 20° C. After one hour's stirring the crystalline product is separated off by filtration, washed with water to remove any salts, washed again with about 100 liters of acetone and finally dried in vacuo.

116 kg (90%) of ethyl {[4-(3-{4-[1-(4-hydroxy-phenyl)-1-methyl-ethyl]-phenoxymethyl}-benzyloxy)-phenyl]-imino-methyl}-carbaminate are obtained.

What is claimed is:

1. A process for preparing a compound of the formula (I)

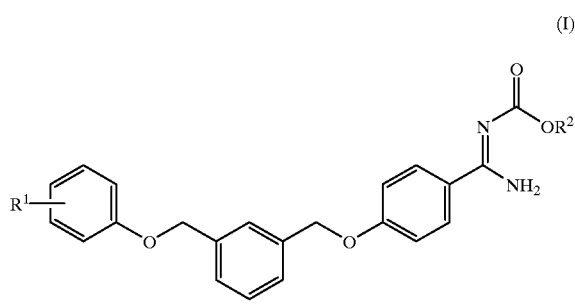

(I)

wherein

R¹ denotes a group selected from among methyl, ethyl, propyl, cyclopentyl, cyclohexyl, phenyl, benzyl and —C(Me₂)phenyl, each of which is optionally mono-, di- or trisubstituted by hydroxy;

R² denotes a group selected from among methyl, ethyl, propyl and benzyl, which process comprises the following steps:

(a) reacting a compound of the formula (II)

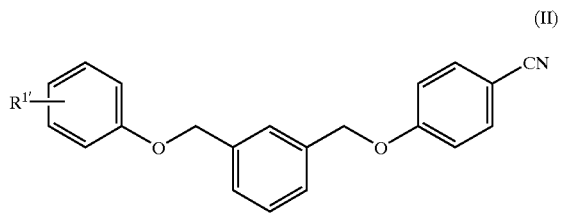

(II)

wherein

R¹' denotes a group selected from among methyl, ethyl, propyl, cyclopentyl, cyclohexyl, phenyl, benzyl and —C(Me₂)phenyl, each of which is optionally mono-, di- or trisubstituted by a group —O—PG, the group —O—PG denoting a protected hydroxyl function selected from among methoxymethyloxy, 2-methoxyethoxymethyloxy, 1-ethoxyethyloxy, 2-tetrahydropyranyloxy, 1-butoxyethyloxy, tert.-butyloxy, benzyloxy and 4-methoxybenzyloxy, with an alkali metal hexaalkyldisilazane of the formula (VIII)

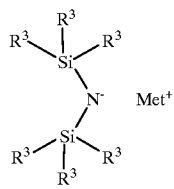

(VIII)

wherein
Met denotes an alkali metal, and
$R^3$ independently in each case denotes a $C_{1-4}$-alkyl group;
(b) treating the product of step (a) with a compound of the formula (III)

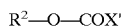

$R^2$—O—COX'                (III)

wherein:
$R^2$ is as hereinbefore defined in this claim and
X' denotes chlorine, bromine or —O—$R^2$, wherein $R^2$ is as hereinbefore defined in this claim;
(c) treating the product of step (b) with a protic acid of formula HY, wherein Y denotes the counter ion, to yield a compound of the formula (IV)

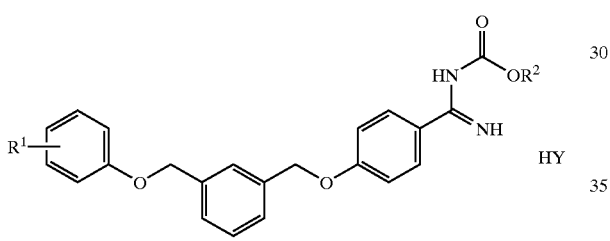

(IV)

or a tautomer thereof, wherein the groups $R^1$, $R^2$ and Y are as hereinbefore defined in this claim;
(d) isolating the compound of the formula IV produced in step (c);
(e) treating the isolated compound of the formula IV, produced in step (d) with a base to produce the compound of the formula I.

2. The process according to claim 1, wherein:
(a) in the compound of formula I,
$R^1$ denotes a group selected from among phenyl, benzyl and —C(Me$_2$)phenyl, each of which is optionally mono- or disubstituted by hydroxy;
$R^2$ denotes a group selected from among ethyl, propyl and benzyl;
(b) in the compound of formula II,
$R^{1'}$ denotes a group selected from among phenyl, benzyl and —C(Me$_2$)phenyl, each of which is optionally mono- or disubstituted by a group —O—PG, the group —O—PG denoting a protected hydroxyl function selected from among methoxymethyloxy, 2-methoxyethoxymethyloxy, 1-ethoxyethyloxy, 2-tetrahydropyranyloxy, 1-butoxyethyloxy, tert.-butyloxy, benzyloxy and 4-methoxybenzyloxy;
(c) in the compound of formula III,
$R^2$ is as hereinbefore defined in this claim, and
X' denotes a chlorine or bromine atom or the group —OR$^2$, wherein $R^2$ is as hereinbefore defined in this claim; and, (d) the acid HY is hydrochloric acid and the intermediate produced in step (c) is a compound of the formula IVA

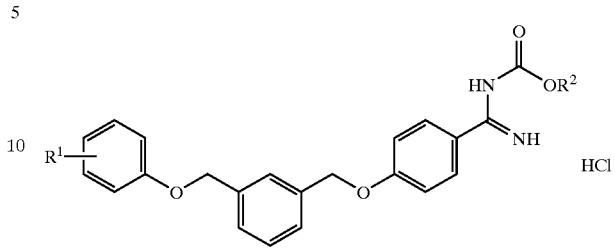

(IVA)

or a tautomer thereof, wherein the groups $R^1$, $R^2$ and Y are as hereinbefore defined in this claim.

3. The process according to claim 1, wherein:

(a) in the compound of formula I,
$R^1$ denotes —C(Me$_2$)phenyl, which is optionally mono-substituted by hydroxy;
$R^2$ denotes ethyl;
(b) in the compound of formula II,
$R^{1'}$ denotes —C(Me$_2$)phenyl, which is optionally mono-substituted by a group —O—PG, the group —O—PG denoting a protected hydroxyl function selected from among methoxymethyloxy, 2-tetrahydropyranyloxy, 1-butoxyethyloxy, tert.-butyloxy, benzyloxy and 4-methoxybenzyloxy; and,
(c) in the compound of formula III,
$R^2$ is as hereinbefore defined in this claim, and
X' denotes a chlorine or bromine atom or the group —OR$^2$, wherein $R^2$ is as hereinbefore defined in this claim.

4. A process for preparing a compound of formula II

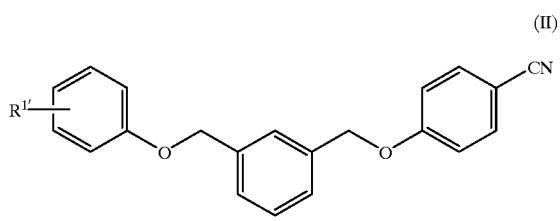

(II)

which process comprises the following steps:

(a) reacting a $C_{1-4}$-alkyl 3-halomethylbenzoate of the formula

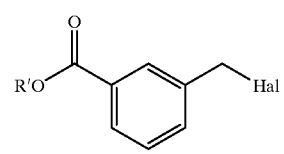

wherein R' denotes a $C_{1-4}$-alkyl group and Hal denotes a halogen atom, with 4-hydroxybenzonitrile

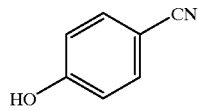

in the manner of a Wilkinson ether synthesis;

(b) reductively converting the resulting alkyl 3-(4-cyano-phenoxy)benzoate of the formula VII

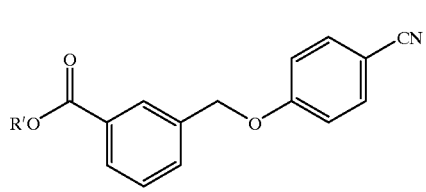

(VII)

wherein R' is as hereinbefore defined in this claim, into a compound of the formula (V)

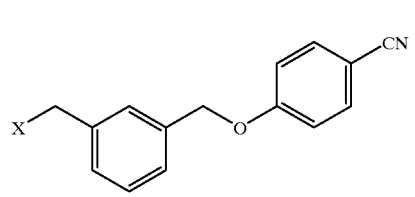

(V)

wherein X denotes hydroxy;

(c) optionally treating the compound of formula (V) wherein X denotes hydroxy with a chlorinating or brominating reagent or a sulphonic acid chloride (selected from methane sulfonic acid chloride, trifluoromethane sulfonic acid chloride and paratoluene sulfonic acid chloride), to yield a compound of the formula V wherein X denotes chlorine, bromine, mesylate, triflate or tosylate; and, (d) reacting the compound of formula (V) wherein X denotes hydroxy, chlorine, bromine, mesylate, triflate or tosylate, with a phenol derivative of formula (VI)

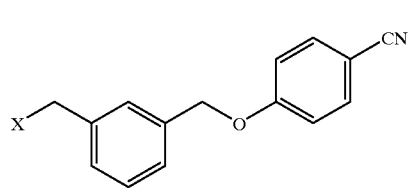

(VI)

wherein $R^{1'}$ denotes a group selected from among methyl, ethyl, propyl, cyclopentyl, cyclohexyl, phenyl, benzyl and —C(Me$_2$)phenyl, each of which is optionally mono-, di- or trisubstituted by a group —O—PG, the group —O—PG denoting a protected hydroxyl function selected from among methoxymethyloxy, 2-methoxyethoxymethyloxy, 1-ethoxyethyloxy, 2-tetrahydropyranyloxy, 1-butoxyethyloxy, tert.-butyloxy, benzyloxy and 4-methoxybenzyloxy; and wherein said phenol derivative of the formula VI is optionally in the form of the corresponding sodium or potassium phenoxide, under basic reaction conditions, in a polar organic solvent, to yield a compound of the formula II.

5. A compound of the formula formula (V),

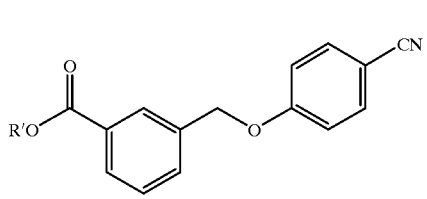

(V)

wherein X denotes hydroxy, chlorine, bromine, mesylate, triflate or tosylate.

6. A compound according to claim 5, wherein X denotes hydroxy or chlorine.

7. A compound of the formula (VII)

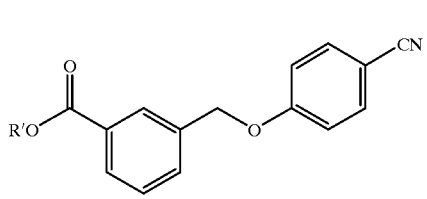

(VII)

wherein R' denotes $C_{1-4}$-alkyl.

* * * * *